United States Patent
Truong (10) Patent No.: US 6,264,119 B1
(45) Date of Patent: Jul. 24, 2001

(54) WATER FILTER SPRAY NOZZLE CLEANING SYSTEM

(75) Inventor: David Truong, San Jose, CA (US)

(73) Assignee: International Business Technology Corporation, San Jose, CA (US)

( * ) Notice: Subject to any disclaimer, the term of this patent is extended or adjusted under 35 U.S.C. 154(b) by 0 days.

(21) Appl. No.: 09/316,971

(22) Filed: May 24, 1999

(51) Int. Cl.[7] .................................................. A62C 5/02
(52) U.S. Cl. ..................... 239/310; 239/317; 239/575; 239/530; 15/29; 601/165; 401/42; 433/88; 433/89
(58) Field of Search ........................... 239/310, 575, 239/530, 317; 15/29, 24; 601/162, 163, 164, 165, 166; 401/40, 42; 433/80, 88, 89

(56) References Cited

U.S. PATENT DOCUMENTS

| | | | |
|---|---|---|---|
| 1,278,225 | * | 9/1918 | Schamberg ........................ 401/42 |
| 1,582,225 | * | 4/1926 | Pulkinghorn ...................... 239/310 |
| 1,827,502 | * | 10/1931 | Alland ............................ 239/310 |
| 1,993,923 | * | 3/1935 | Eccardt .......................... 239/310 |
| 2,266,902 | * | 12/1941 | Perkins .......................... 239/310 |
| 2,302,799 | * | 11/1942 | Peterson ......................... 239/310 |
| 2,624,619 | * | 1/1953 | Fletcher et al. .................. 239/310 |
| 3,509,874 | * | 5/1970 | Stillman ......................... 15/24 |
| 3,593,707 | * | 7/1971 | Pifer ............................ 601/163 |
| 3,776,468 | * | 12/1973 | Davenport ........................ 239/310 |
| 3,869,746 | * | 3/1975 | Man-king ......................... 15/29 |
| 3,917,172 | * | 11/1975 | O'Hare ........................... 239/575 |
| 4,181,997 | * | 1/1980 | O'Rourke ......................... 15/24 |
| 4,335,481 | * | 6/1982 | Slayman .......................... 15/29 |
| 4,564,005 | * | 1/1986 | Marchand et al. .................. 601/165 |
| 4,650,470 | * | 3/1987 | Epstein .......................... 239/310 |
| 5,220,914 | * | 6/1993 | Thompson ......................... 601/162 |
| 5,387,182 | * | 2/1995 | Otani ............................ 601/165 |
| 5,484,281 | * | 1/1996 | Renow et al. ..................... 601/162 |
| 5,500,973 | * | 3/1996 | Phelan ........................... 15/29 |
| 5,626,472 | * | 5/1997 | Pennetta ......................... 601/162 |

* cited by examiner

Primary Examiner—David A. Scherbel
Assistant Examiner—Dinh Q. Nguyen
(74) Attorney, Agent, or Firm—Beyer Weaver & Thomas, LLP (57) ABSTRACT

Methods and apparatus for generating a small, maneuverable stream of filtered fluid without benefit of a pump or electrical power are disclosed. According to one aspect of the present invention, a spray nozzle apparatus for dispensing a maneuverable stream of fluid, that originates from a fluid source at a first pressure includes an adapter assembly, a nozzle subassembly, and a flexible tubing. The adapter assembly is mechanically coupled to the fluid source, and is arranged to allow the fluid to flow from the fluid source through the adapter assembly. The nozzle subassembly dispenses the fluid at a second pressure, and includes a fluid intake end and a fluid dispensing end. The fluid dispensing end allows the fluid to flow therethrough in a small, stream-like configuration at the second pressure, and is in fluid communication with the adapter assembly. The flexible tubing allows the fluid to flow through, and is coupled to the fluid intake end of the nozzle subassembly. In one embodiment, the spray nozzle apparatus includes a filter that is in fluid communication with the flexible tubing and the adapter assembly.

39 Claims, 7 Drawing Sheets

WATER FILTER SPRAY NOZZLE CLEANING SYSTEM

BACKGROUND OF THE INVENTION

1. Field of Invention

The present invention relates generally to methods and apparatus for use in cleaning objects using a fluid-based solution. More particularly, the present invention relates to methods and apparatus for providing a stream of water through the use of a filtering nozzle assembly that can be attached to a faucet.

2. Description of the Related Art

In the area of personal care, as well as in many other areas including, but not limited to, the cleaning of small parts, the ability to provide and to maneuver a small jet of water is desirable. This ability to maneuver a small jet, or stream, of water generally enables the water to be accurately directed at a specific location. By way of example, a small, maneuverable jet of water may be readily directed at a specific target area, thereby enabling the target area to receive the water without wetting surrounding areas.

A maneuverable jet of water is the particularly useful in the area of personal care, e.g., as it pertains to dental hygiene. While personal care products which provide maneuverable jets of water are available, these products typically involve the use or either, or both, electricity and an associated mechanism arranged to pump water. One personal care product intended for dental use is the Water Pik® Personal Dental System, which is a dental appliance that is available commercially from Teledyne Water Pik of Fort Collins, Colo. The Water Pik® Personal Dental System is designed to enable a user to direct a jet of water at his or her teeth in order to dislodge any food particles which may have become lodged around or between his or her teeth. In order to use a Water Pik® Personal Dental System, or a similar system, a user is required add water to a reservoir, which is a part of the system, then provide power, i.e., electricity, to the system in order to activate a pump which pumps water from the reservoir through a hand-held nozzle mechanism. A stream of water is then discharged through the hand-held nozzle mechanism.

While a system such as the Water Pik® Personal Dental System provides a stream of water which a user can maneuver, the use such a system typically involves a large amount of set-up time and effort in order to ready the system for use. Among other set-up tasks, a user must locate an electrical outlet which may be used to power the system. The fact that an electrical outlet must be present in order for the system to be used serves to reduce the portability of the system, thereby limiting the use of the system.

Further, the user must transfer water to the system reservoir from a water source, e.g., a faucet. As the water in the reservoir is used, i.e., as the water in the reservoir empties, the user must add more water to the reservoir in order to continue using the system. Having a supply of water which must repeatedly be replenished increases the overall set-up time, and maintenance time, required to prepare the system for use.

Adjusting the temperature of water used in a system such as the Water Pik® Personal Dental System is also time-consuming. Such a system typically does not provide either a heating mechanism or a cooling mechanism which may be used to vary the temperature of water that is through a hand-held nozzle mechanism of the system. In other words, the system does not provide a user with the ability to vary the temperature of the water in the system. The temperature of water discharged through the hand-held nozzle mechanism is dependent upon the temperature of the water in the system reservoir. Typically, the temperature of the water discharged from the nozzle mechanism is approximately the same as the temperature of the water in the system reservoir. Due to the inability to vary the temperature of the water, it follows that if a user discovers that the temperature of the water in the system reservoir is unsatisfactory, e.g, too hot, in order to correct the situation, the user must either add water of a different temperature to the system reservoir to change the overall temperature of the water in the system reservoir, completely purge and replace the water in the reservoir, or wait until enough time elapses for the water in the system reservoir to be sufficiently cooled. Clearly, the process of achieving a satisfactory water temperature often proves to be rather inefficient.

Since most systems like the Water Pik® Personal Dental System include a pump, some fluids, e.g., salt water, may not be used in the systems due to reliability issues with the pump. Additionally, particulate matter that may be present in water or any other fluid made cause the pump to wear out or otherwise malfunction.

In addition to being useful in the area of personal hygiene, a maneuverable jet of water is also useful in applications involving the cleaning of small tools, as for example jewelry making tools, and small parts, as for example the delicate parts used in making watches. Being able to control a small jet of water provides a user with the ability to clean small tools and parts with some measure of precision. Small, maneuverable jets of water are also typically used in laboratory applications and horticultural applications, as well as many other applications. However, as small, maneuverable jets of water are typically generated by electrical appliances, the use of the small, maneuverable jets of water is somewhat limited in that they may only be used in the proximity of a power source.

In view of the foregoing, there are desired improved methods and apparatus for use in efficiently producing a maneuverable stream of water without requiring a power source or an associated mechanism for pumping water.

SUMMARY OF THE INVENTION

The present invention relates generally to a filtering spray nozzle assembly which is suitable for coupling to a faucet. According to one aspect of the present invention, a spray nozzle apparatus for dispensing a maneuverable stream of fluid, that originates from a fluid source at a first pressure includes an adapter assembly, a nozzle subassembly, and a flexible tubing. The adapter assembly is mechanically coupled to the fluid source, and is arranged to allow the fluid to flow from the fluid source through the adapter assembly. The nozzle subassembly dispenses the fluid at a second pressure, and includes a fluid intake end and a fluid dispensing end. The fluid dispensing end allows the fluid to flow therethrough in a small, stream-like configuration at the second pressure, and is in fluid communication with the adapter assembly. The flexible tubing allows the fluid to flow through, and is coupled to the fluid intake end of the nozzle subassembly.

In one embodiment, the spray nozzle apparatus includes a filter that is in fluid communication with the flexible tubing and the adapter assembly. The filter allows the fluid to flow therethrough, and also filters particulate matter from the fluid when the fluid flows therethrough. In another embodiment, the adapter assembly includes an outlet coupler, the outlet coupler that is arranged to be coupled to the fluid source, an inlet that is in fluid communication with the nozzle subassembly, a bypass outlet being that permits the fluid to flow through, and a valve that controls the flow of the fluid through the inlet and through the bypass outlet.

According to another aspect of the present invention, a method for providing a small, maneuverable stream of fluid includes providing fluid originating from a fluid source, providing a nozzle assembly, and providing an adapter assembly. The nozzle assembly includes a body and a fluid dispensing extension that is coupled to the body. The nozzle assembly is arranged to dispense the stream of fluid through the fluid dispensing extension. The adapter assembly is arranged to mechanically couple the fluid source faucet with the nozzle assembly. In one embodiment, the method includes filtering the fluid removes at least some undesirable particles from the fluid.

These and other advantages of the present invention will become apparent upon reading the following detailed descriptions and studying the various figures of the drawings.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE EMBODIMENTS

The present invention will now be described in detail with reference to a few preferred embodiments thereof as illustrated in the accompanying drawings. In the following description, numerous specific details are set forth in order to provide a thorough understanding of the present invention. It will be obvious, however, to one skilled in the art, that the present invention may be practiced without some or all of these specific details. In other instances, well known structures and steps have not been described in detail in order not to unnecessarily obscure the present invention.

A fluid jet dispensing apparatus, or a spray nozzle assembly, that may be coupled to a water faucet, or similar fluid supply outlet, enables a small, maneuverable stream of fluid to be generated from virtually any faucet, through the use of an adapter mechanism. Such an apparatus is portable in that the apparatus enables a maneuverable stream of the fluid to be dispensed from any faucet without requiring the use of a dedicated pumping mechanism or an electrical power source that is linked with the apparatus. A spray nozzle assembly that may be mechanically coupled to a water faucet, for example, enables the temperature of the stream of fluid that is expelled from the nozzle assembly to be readily varied to meet the requirements of a particular application without requiring any additional temperature adjustment mechanisms. The ability to vary the temperature of the fluid stems from the fact that faucets typically already provide sources of cold water and hot water that may be co-mingled in order to adjust the overall temperature of water flowing from a faucet. In addition, since faucets generally also already enable the pressure of out-flowing fluid to be altered, a nozzle assembly that can be coupled to a faucet may take advantage of this pressure-altering feature. Hence, the range of pressures of fluid that passes out of the nozzle assembly is relatively large, and may easily be varied.

A spray nozzle assembly that does not require the use of a dedicated pumping mechanism or an electrical power source also enables a greater number of different fluids to be used with the spray nozzle assembly. For example, due to reliability issues such as corrosion concerns, salt water generally may not be used with a pumping mechanism. A fluid such as salt water, however, may be used with the spray nozzle assembly that does not include a dedicated pumping mechanism.

Figure 1:
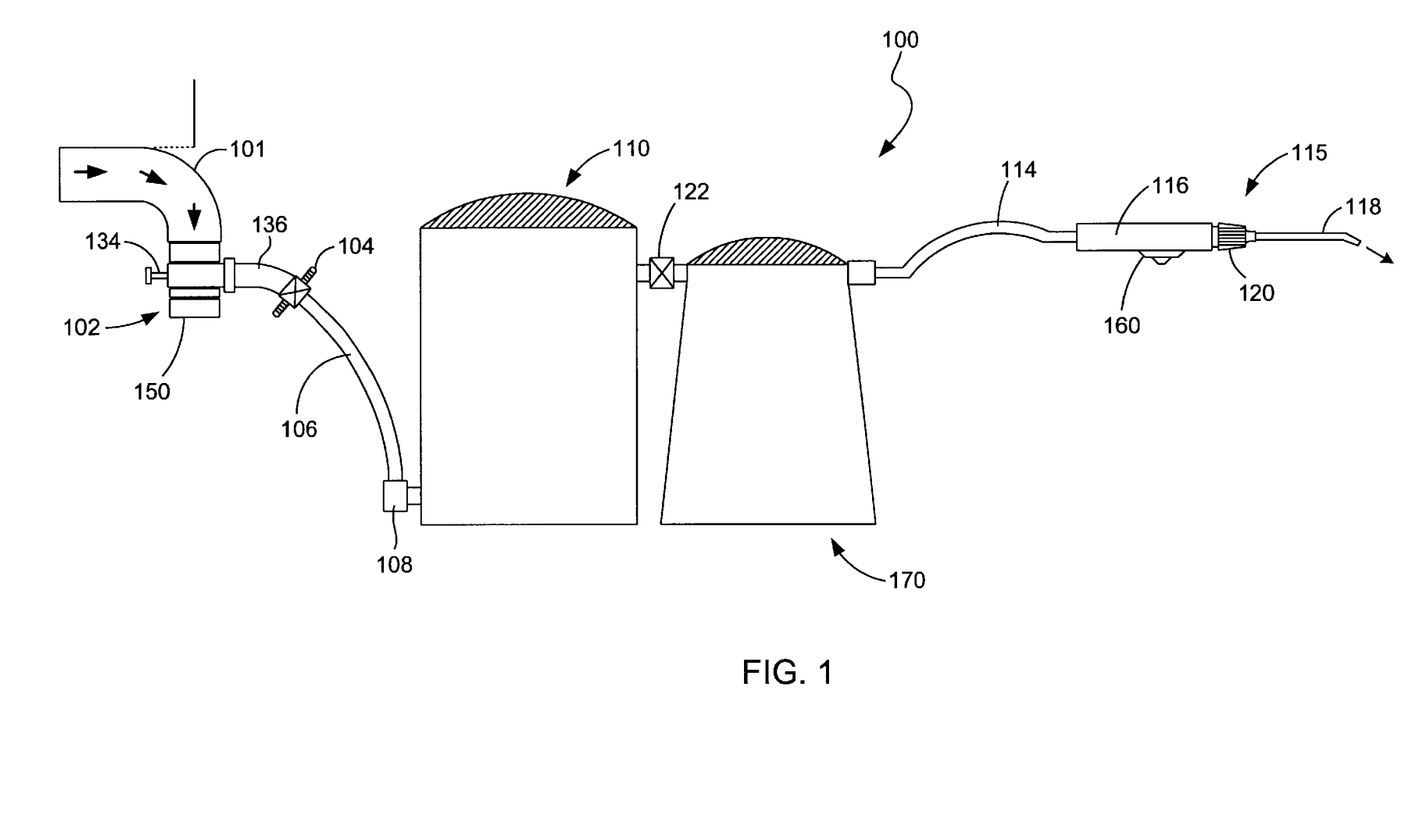
FIG. 1 is a diagrammatic representation of a filtering spray nozzle cleaning assembly coupled to a fluid supply faucet in accordance with an embodiment of the present invention.

Referring initially to FIG. 1, there is shown a filtering spray nozzle system with an adapter, in accordance with an embodiment of the present invention. Spray nozzle system 100 includes a nozzle subassembly 115. Nozzle subassembly 115 includes a body 116, e.g., a handle, and a fluid dispensing extension 118 that is coupled to body 116 through a coupler 120. While coupler 120 is shown as being integral to fluid dispensing extension 118 such that coupler may either be press-fit, screwed into, or otherwise engaged with an end of body 116, it should be appreciated that coupler 120 may not be integrated into fluid dispensing extension 118.

Body 116 is sized such that it may be comfortably gripped in a hand, and optionally serves as an intermediate reservoir for holding fluid prior to passing fluid to fluid dispensing extension 118. While any appropriate material may be used to form body 116, materials which are robust, lightweight and water-resistant, as for example plastic, are preferred.

In the embodiment as shown, fluid dispensing extension 118 is a semi-rigid tube with a tip portion that may be tapered with respect to a base portion of fluid dispensing extension 118. In other words, fluid dispensing extension 118 is configured as a nozzle. As such, fluid entering fluid dispensing extension 118 at its base will generally be at a lower pressure than fluid exiting its tip. Fluid dispensing extension 118 will be described in more detail below with respect to FIG. 4. Other embodiments of a suitable fluid dispensing extension that may be used as a part of nozzle subassembly 115 will be discussed below with reference to FIGS. 5a–5e.

When fluid, e.g., water, flows through nozzle subassembly 115 an actuator 160, which is a part of a controller mechanism (not shown) that is internal to body 116, may be "turned on," or activated, to enable the fluid to flow through fluid dispensing extension 118 and to be expelled from the tip of fluid dispensing extension 118 in a stream-like configuration. Alternatively, actuator 160 may be "turned off," or deactivated, to inhibit the flow of fluid through fluid dispensing extension 118. In one embodiment, actuator 160 is a button or a switch, and the controller of which actuator 160 is a part may be composed of a hinge which alternately exposes and blocks off fluid dispensing extension 118 with respect to body 116. It should be appreciated that in general, by varying the pressure or the force exerted on actuator 160 by a finger or thumb, the pressure of the fluid expelled from fluid dispensing extension 118 may be varied.

Spray nozzle system 100 is arranged such that the fluid which is expelled in a stream-like configuration from the tip of fluid dispensing extension 118 is provided by a fluid source such as a faucet. In other words, spray nozzle system 100 is coupled to a faucet 101 that supplies fluid, e.g., a water faucet which supplies water. The flow of fluid through faucet 101 is generally controlled by a handle or handles (not shown) which control, in one embodiment, the pressure of the flow and the temperature of the flow. As mentioned above, the pressure of the flow may further be controlled using actuator 160.

An outlet coupling system 102, referred to herein as an adapter assembly or an adapter, is sized to be engaged with faucet 101. Adapter 102 includes a valve 134, a post 150, and a system inlet 136, as shown. Valve 134 has a "closed" position and an "open" position. When valve 134 is in a closed position, then fluid flows substantially only from faucet 101 through to nozzle subassembly 115. Alternatively, when valve 134 is in an open position, then fluid flows through post 150. It should be appreciated that when actuator 160 is arranged to prevent flow of fluid through fluid dispensing extension 118, i.e., when actuator 160 blocks off fluid dispensing extension 118 with respect to body 116, then valve 134 may automatically open to enable fluid to flow through post 150. In other words, valve 134 may be a "bypass" valve. Valve 134 also enables spray nozzle system 100 to remain coupled to faucet 101 without significantly affecting "normal" use of faucet 101. That is, faucet 101 effectively does not have to be dedicated for use with spray nozzle system 100 even when spray nozzle system 100 is attached to faucet 101.

Through system inlet 136, fluid flows past a coupler 104 and through a hose 106. Hose 106, which is typically a flexible tube, may be made from any suitable material, as for example a rubber material or a malleable plastic material. Some rubber materials have been observed to shrink significantly, thereby causing problems with fluid flow through the tubing, whereas plastic materials, e.g. plastic cables, have generally been observed to be relatively immune from significant shrinkage. Therefore, hose 106 is generally formed from a plastic material. Coupler 104 is arranged to enable spray nozzle assembly 100 to be readily disassembled and assembled, e.g., coupler 104 may be a snap-lock. Through a coupler 108, hose is coupled to a filter 110 that is arranged to filter fluid provided by faucet 101. One suitable filter 110 will be described below with respect to FIG. 2.

In the embodiment as shown, filter 110 is coupled to a sprayer 170 through a coupler 122. As will be appreciated by those skilled in the art, the design of coupler 122, coupler 104 and coupler 108 may vary widely. By way of example, coupler 108 may be a snap adapter which includes a valve that enables the flow of fluid through spray nozzle system 100 to be controlled. When such a valve is closed, the flow of fluid through spray nozzle system 100 may be stopped at coupler 108. Such a valve, when open, may serve to prevent pressure from building within hose 106 when valve 134 is in an open position.

Generally, a coupler may include two portions. One portion may be a male portion that is arranged to engage a second portion that is a female portion. For example, hose 106 may be substantially fixed to a male end of coupler 104 and a male end of coupler 108. The male end of coupler 104 may be engaged with, e.g., snapped into, a female end of coupler 104 which is substantially fixed to system inlet 136. Likewise, the male end of coupler 108 may be engaged with a female end of coupler 108 which is substantially fixed to filter 110.

Sprayer 170 holds a liquid such as, for example, a water-soluble solution or a cleaning solution, and is arranged to allow filtered fluid to mix with the liquid in sprayer 170. Sprayer 170 will be discussed below with reference to FIG. 3. Once fluid, i.e., the mixture of filtered fluid and the liquid held by sprayer 170, passes through sprayer 170, it then passes through hose 114 to nozzle subassembly 115. Like hose 106, hose 114 is typically formed from a malleable plastic material.

Figure 2:
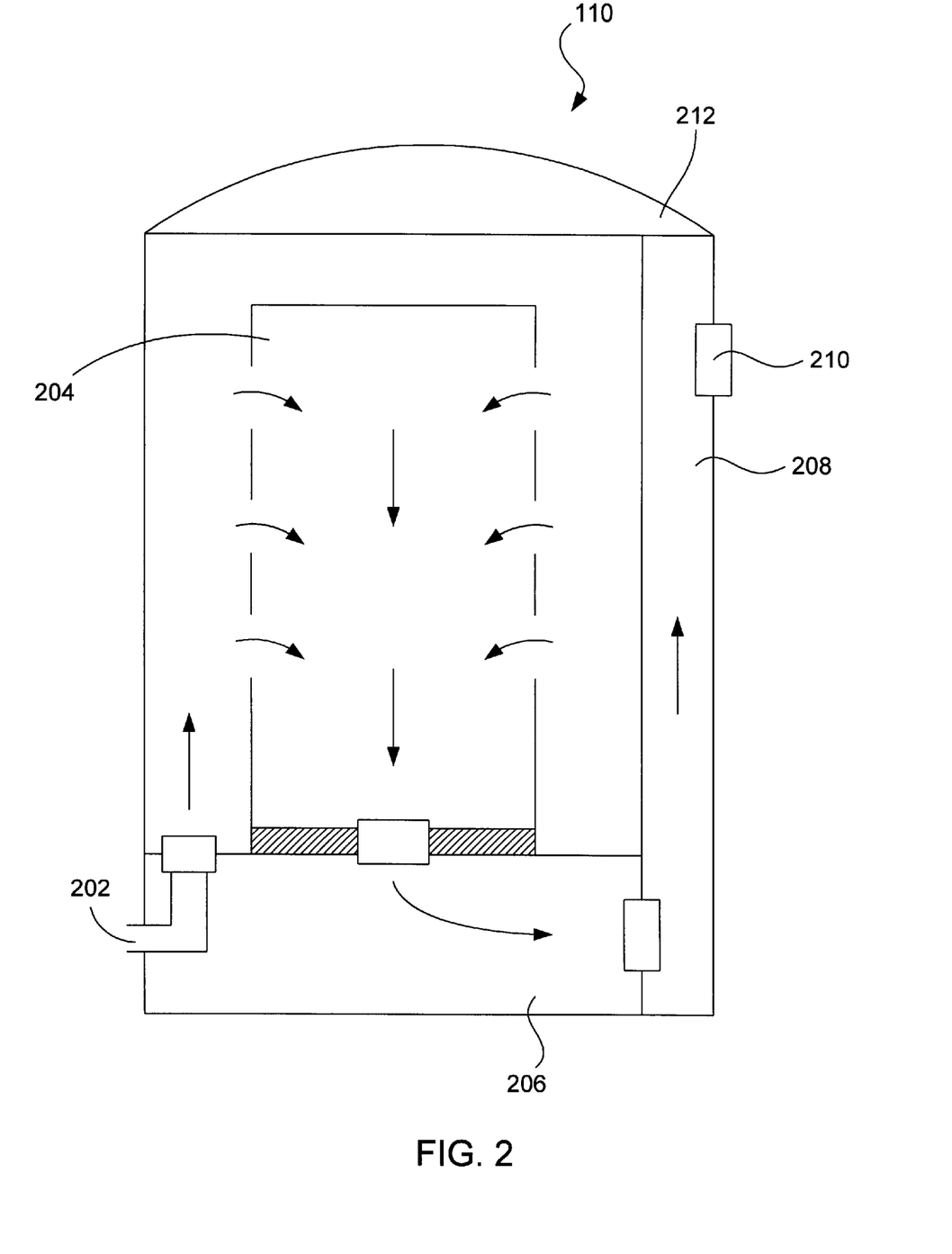
FIG. 2 is a diagrammatic representation of a filtering assembly, i.e., filter 110 of FIG. 1, in accordance with an embodiment of the present invention.

FIG. 2 is a diagrammatic representation of a filtering assembly, i.e., filter 110 of FIG. 1, in accordance with an embodiment of the present invention. Filter 110 is arranged to eliminate some particulate matter from fluid as the fluid flows through filter 110. Eliminating particulate matter from fluid enables the fluid which is ejected from an overall spray nozzle system to be essentially "pure," e.g., substantially free of particles. Providing substantially particle-free fluid prevents damage from occurring in cleaning applications, as particles may often scratch or otherwise damage objects which are being cleaned. Such particles, e.g., sand particles, or residue that is present in pipes such as water pipes are often present in fluid.

Filter 110 includes an inlet portion 202 which receives fluid provided by faucet 101 through adapter assembly 102 of FIG. 1. It should be appreciated that various arrows have been shown in FIG. 2 to indicate the general flow of fluid, e.g., water, through filter . Fluid flows from inlet portion 202 through to a filtering cartridge 204. In one embodiment, filtering cartridge 204 includes a mesh-like screen arrangement (not shown) which is arranged to trap particles. The size of the particles which a re trapped is dependent upon the size of the openings in the mesh-like screen arrangement. Once the fluid is filtered and passed through filtering cartridge 204, the fluid then passes into a reservoir 206, and, subsequently, through a delivery pathway 208 to an outlet portion 210. Outlet portion 210 is arranged to be coupled to coupler 122, as shown in FIG. 1.

In the described embodiment, in order to facilitate the changing of filtering cartridge 204 once filtering cartridge 204 is full, i.e., contains a relatively large amount of particles, filter 110 may include a removable cap 212. Cap 212 may be removed such that filtering cartridge 204 may be readily replaced with a new filtering cartridge as necessary. In alternate embodiments, however, it should be appreciated that rather than replacing filtering cartridge 204, the entire filter 110 may be replaced.

As mentioned above with respect to FIG. 1, spray nozzle system 100 may include a sprayer 170 that contains a solution which is to be mixed with fluid provided by faucet 101. When spray nozzle system 100 is to be used for a purpose such as cleaning laboratory instruments, the solution contained in sprayer 170 may be a cleaning solution, e.g. a soap solution, that is easily mixed with the fluid provided by faucet 101. Alternatively, when spray nozzle system 100 is to be used for purposes of dental hygiene, then sprayer 170 may contain a fluoride or an antiseptic solution.

Figure 3:
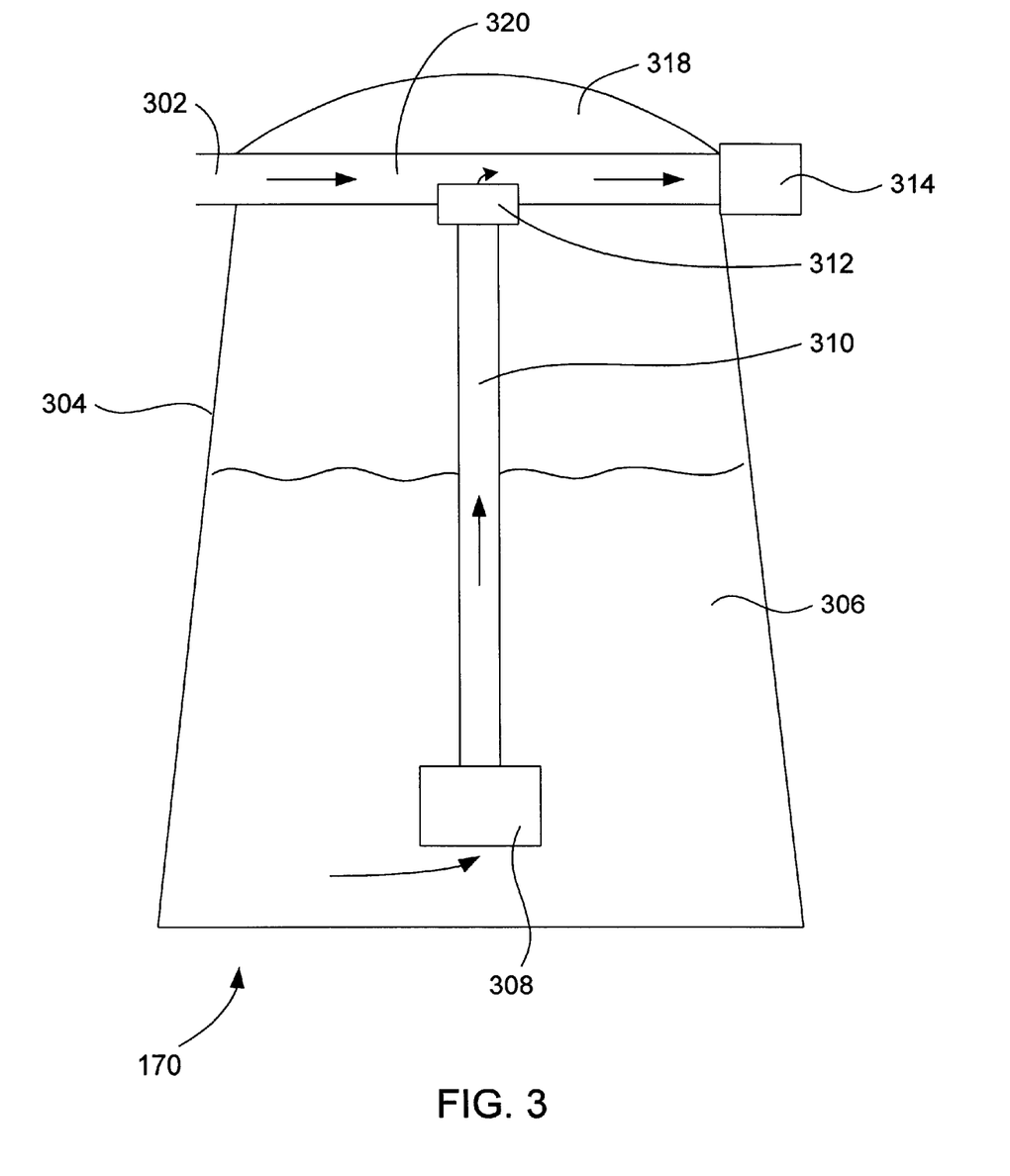
FIG. 3 is a diagrammatic representation of a sprayer, i.e., sprayer 170 of FIG. 1, in accordance with an embodiment of the present invention.

FIG. 3 is a diagrammatic representation of a sprayer, i.e., sprayer 170 of FIG. 1, in accordance with an embodiment of the present invention. In the described embodiment, sprayer 170 includes an inlet 302 which is arranged to receive filtered fluid from filter 110 through coupler 122 of FIG. 1. Sprayer 170 includes a reservoir section 304 that is arranged to hold substantially any liquid 306 which is intended to be mixed with the fluid that flows into inlet 302.

By activating a button (not shown) in sprayer top 318, a sprayer pump arrangement 312 pumps liquid 306 through a pump outlet 312 and into a mix hose 320 where liquid 306 is effectively mixed with the fluid passed from filter 110 of FIGS. 1 and 2. It should be understood that sprayer 170 or, more particularly, the button in sprayer top 318 and sprayer pump arrangement 312, operates in substantially the same manner as a standard spray bottle. As shown, sprayer pump arrangement 312 is coupled through a pipe 310 to a filter 308 which filters particles from liquid 306. Mix hose 320 includes an outlet 314 which may be attached or otherwise coupled to a tube or hose which is further coupled to a nozzle subassembly, e.g., nozzle subassembly 115 of FIG. 1. Specifically, outlet 314 may be coupled to a portion of a coupler, e. a female portion of a snap adapter, that is arranged to engage a portion of a coupler which is substantially fixed to a tube or hose.

In one embodiment, sprayer top 318 may include a dial (not shown) which is arranged to control the amount of liquid 306 which is mixed with a fluid flowing through mix hose 320. Such a dial may be coupled to a valve (not shown), for example, which controls the amount of fluid that flows through sprayer pump arrangement 312.

Sprayer top 318 is typically arranged to be removed such that the supply of fluid 306 may be easily replenished or replaced. Sprayer top 318 may be arranged to be screwed and unscrewed with respect to reservoir 304. Alternatively, sprayer top 318 may be arranged to be snapped into and unsnapped from reservoir 304.

Figure 4:
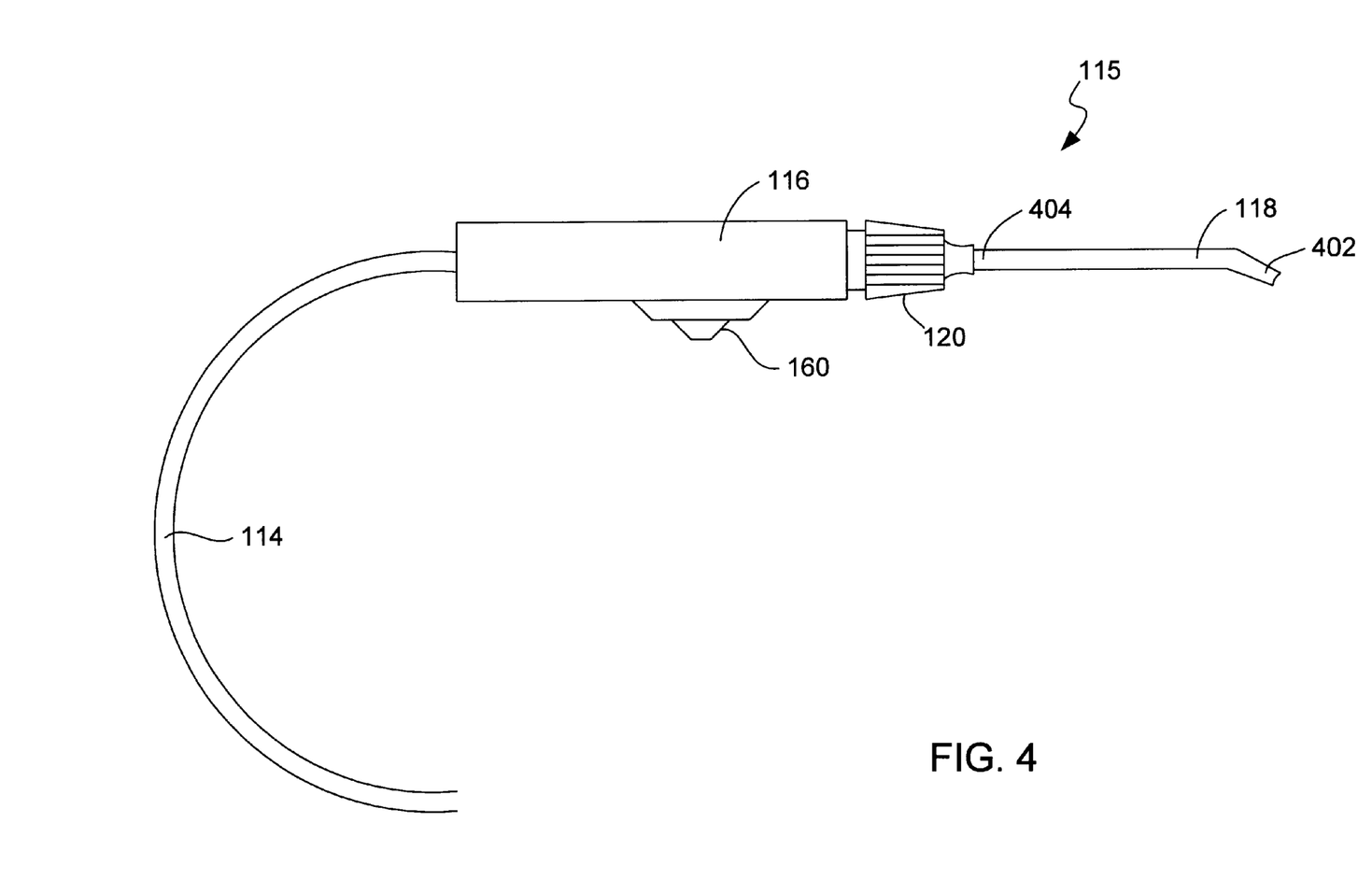
FIG. 4 is a diagrammatic representation of a spray nozzle subassembly, i.e., spray nozzle subassembly 115 of FIG. 1, in accordance with an embodiment of the present invention.

In general, the fluid dispensing extension of a nozzle subassembly used in ail overall spray nozzle system may tame on a variety of different configurations. Referring next to FIG. 4, one embodiment of a fluid dispensing extension, i.e., fluid dispensing extension 118 of FIG. 1, will be described. As mentioned above with respect to FIG. 1, fluid dispensing extension 118 is a semi-rigid tube. Fluid dispensing extension 118 includes a tip portion 402 that is tapered with respect to a base portion 404 of fluid dispensing extension 118. Since fluid dispensing extension 118 is arranged in a nozzle-like configuration, fluid entering fluid dispensing extension 118 at base portion 404 will generally be at a lower pressure than fluid exiting tip portion 402.

As shown, tip portion 402 is angled with respect to the rest of fluid dispensing extension 118. It should be appreciated, however, that tip portion 402 is not necessarily angled with respect to the rest of fluid dispensing extension 118. That is, fluid dispensing extension 118 may have a substantially straight configuration. Generally, fluid dispensing extension 118 may be formed from any appropriate material. Appropriate materials may include, but are not limited to, lightweight, water-resistant materials like plastic. In particular, in order to enable a user of nozzle subassembly 115 to view fluid passing through fluid dispensing extension 118, fluid dispensing extension 118 may be formed from a translucent plastic material.

Figure 5A:
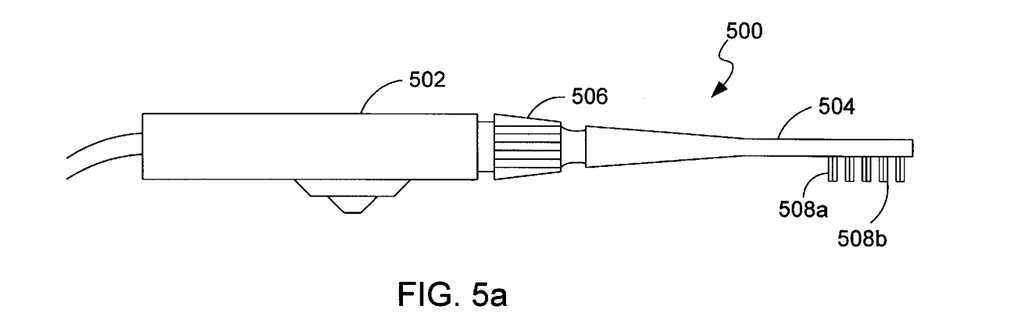
FIG. 5a is a diagrammatic representation of a first brush tip that is suitable for use as a part of a spray nozzle assembly in accordance with another embodiment of the present invention.

In general, a nozzle subassembly or, more particularly, the body of a nozzle subassembly, may be coupled to various fluid dispensing extensions. Since an overall spray nozzle system is often used for cleaning applications, suitable fluid dispensing extensions include brush and polishing arrangements. With reference to FIGS. 5a–5e, various embodiments of brush and polishing arrangements will be described in accordance with the present invention. FIG. 5a is a diagrammatic representation of a nozzle subassembly 500 which includes a body 502 which is coupled to a toothbrush 504 through a coupler 506 that is integral to toothbrush 504. Toothbrush 504 includes bristles 508 and an opening or openings (not shown) through which fluid may flow in a stream-like configuration. Bristles 508 are arranged to brush against teeth, for example, while a user manipulates toothbrush 504 by holding body 502. The water that flows through openings brings the water into contact with the teeth. In one embodiment, each bristle group 508 is associated with a single opening through which water may flow. That is, each bristle group 508a may be positioned to at least partially overlap or be in proximity to an opening that is substantially dedicated to bristle group 508a.

Figure 5B:
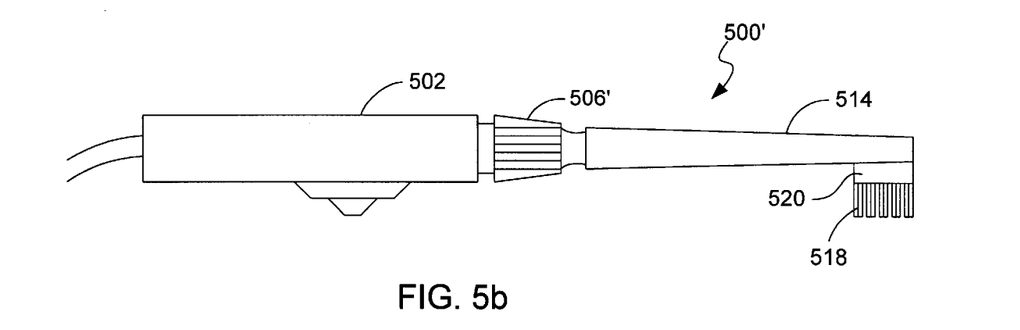
FIG. 5b is a diagrammatic representation of a second brush tip that is suitable for use as a part of a spray nozzle assembly in accordance with still another embodiment of the present invention.

FIG. 5b is a diagrammatic representation of a nozzle subassembly 500' which includes a polisher brush 514. Polisher brush 514 is suitable for use as a tool for dental hygiene. Polisher brush 514 is coupled to body 502 through a coupler 506', and includes bristles 518 that are mounted on a rotatable plate 520. It should be appreciated that in one embodiment, rotatable plate 520 may rotate in response to a jet of water flowing through and against rotatable plate 520. In another embodiment, rotatable plate 520 may rotate when a mechanical actuator is activated through battery power. In such an embodiment, an activator switch may be included on either polisher brush 514 or body 502. One example of a nozzle subassembly that is capable of providing battery power to a polisher brush will be discussed below with reference to FIG. 6.

Polisher brush 514 may be suitable for use in polishing teeth. A sprayer, e.g., sprayer 170 of FIG. 1, that is used with polisher brush 514 may contain a baking powder solution that is used to whiten teeth during a polishing process. The baking powder solution, which may be mixed with filtered water in the mix hose of the sprayer, may be expelled through an opening or openings that pass through rotatable plate 520.

Figure 5C:
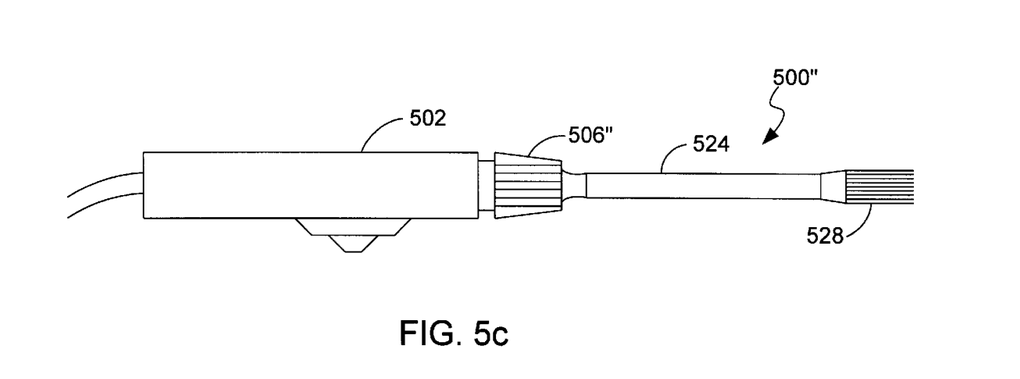
FIG. 5c is a diagrammatic representation of a third brush tip that is suitable for use as a part of a spray nozzle assembly in accordance with yet another embodiment of the present invention.

FIG. 5c is a diagrammatic representation of a nozzle subassembly 500" with a brush 524 that is suitable for use in cleaning tools. Brush 524, which is coupled to body 502 through a coupler 506", includes bristles 528 and holes (not shown) which allows a fluid provided through body 502 to effectively flow between bristles 528. Hence, while bristles 528 are brushed against an object to remove residue from the object, fluid is also provided to wash away the residue.

It should be appreciated that brush 524 may also be used for painting purposes. When brush 524 is used for painting purposes, fluid may be prevented from flowing through brush 524, e.g., by keeping an associated faucet off, until it is desired to clean brush 524. During cleaning of brush 524, allowing fluid to flow through holes in brush 524 may facilitate the cleaning of brush 524.

Figure 5D:
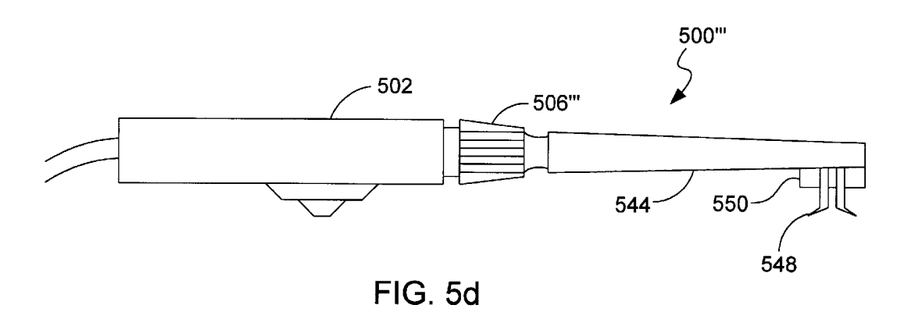
FIG. 5d is a diagrammatic representation of a fourth brush or polisher tip that is suitable for use as a part of a spray nozzle assembly in accordance with another embodiment of the present invention.

FIG. 5*d* is a diagrammatic representation of a nozzle subassembly 500''' with a polisher 544 that is suitable for polishing objects such as teeth. Polisher 544, which is arranged to be coupled to body 502 through a coupler 506''', includes rubber protrusions 548 that are mounted on a rotatable plate 550. Rubber protrusions 548 may surround an opening through which a jet of fluid may flow. Rotatable plate 550 may rotate in response to a jet of water flowing through and against rotatable plate 550. Alternatively, rotatable plate 520 may rotate when a mechanical actuator is activated through battery power, as for example battery power provided by body 502.

Figure 5E:
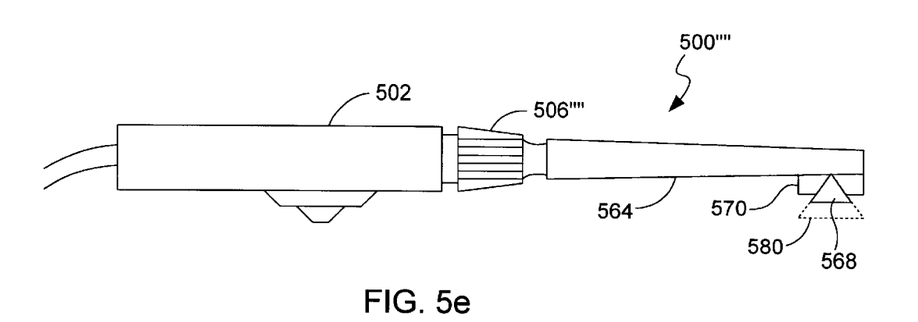
FIG. 5e is a diagrammatic representation of a fifth brush or polisher tip that is suitable for use as a part of a spray nozzle assembly in accordance with still another embodiment of the present invention.

With reference to FIG. 5*e*, a polisher which is arranged to allow fluid to be ejected from the polisher in a conical configuration will be described in accordance with an embodiment of the present invention. A polisher 564, which may be coupled to body 502 through a coupler 506'''', is a part of a nozzle subassembly 500''''. As shown, polisher 564 may include a substantially conical rubber protrusion 568 that is mounted on a rotatable plate 570. Rubber protrusion 568 may rotate to enable an article or object to be polished. In one embodiment, rubber protrusion 568 is seated in an opening through which fluid may flow such that rubber protrusion 568 serves as an obstacle to the fluid flow. In such an embodiment, fluid may effectively flow around rubber protrusion 568, i.e., the stream of fluid flowing from an opening is "separated" to form a conical configuration 580.

Figure 6:
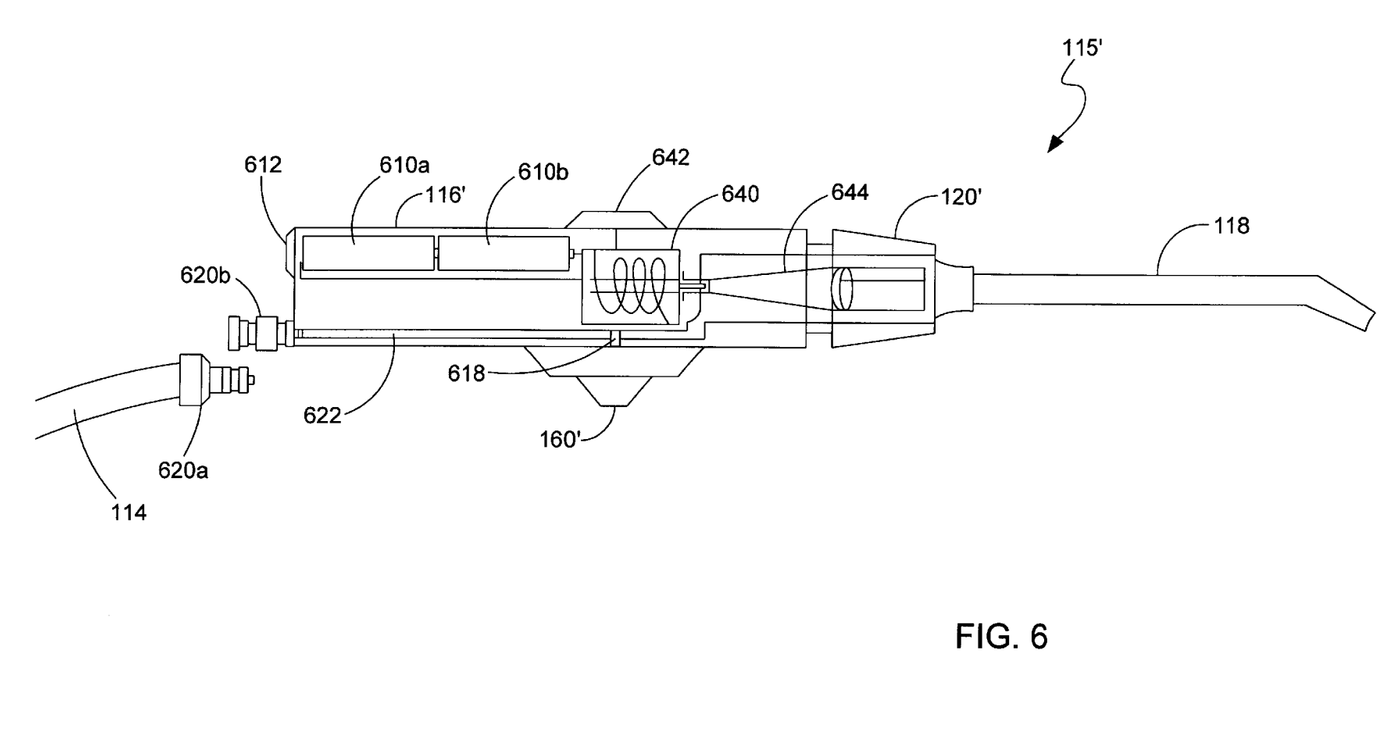
FIG. 6 is a diagrammatic cross-sectional representation of a nozzle subassembly which is motorized in accordance with another embodiment of the present invention.

As mentioned above with respect to FIG. 5*b*, a nozzle subassembly may provide battery power which allows a portion of a brush to rotate. It should be appreciated that the battery power does not affect the flow of fluid through a fluid dispensing extension. In other words, the flow of fluid through a nozzle subassembly is not dependent upon any battery power that is provided. FIG. 6 is a diagrammatic cross-sectional representation of a nozzle subassembly which includes a motor in accordance with an embodiment of the present invention. A nozzle subassembly 115' includes a body 116' and a fluid dispensing extension 118 that is coupled to body 116' through a coupler 120'.

Body 116' is sized such that it may be comfortably gripped in a hand, while accommodating the insertion of batteries 610. It should be appreciated that the size of batteries 610 is at least partially dependent upon the power output required by nozzle subassembly 115'. In the embodiment as shown, batteries 610 are 1.5 Volt batteries, i.e., AA size batteries. Body 116' also includes a cover 612 which may be removed to enable batteries 610 to be inserted into body 116'. Although any appropriate material may be used to form body 116', materials which are robust, lightweight, heat-resistant, and water-resistant, as for example plastic, are preferred.

Batteries 610 are coupled to a motor 640, e.g., a DC motor. Motor 640 is coupled to a switch 642 which is arranged to control power to motor 640. In other words, switch 642 is arranged to turn motor 640 on and off. Motor 640 includes a motor coupler 644 which is arranged to be coupled to a brush, e.g., brush 514 of FIG. 5*b*, which uses electrical power, as will be discussed below.

Nozzle subassembly 115' has been shown as including fluid dispensing extension 118, which is configured as a nozzle. As such, fluid dispensing extension 118 does not use power generated using batteries 610. The flow of fluid through fluid dispensing extension 118 may be controlled by actuator 160' which operates a valve closure 618 that at least partially controls the flow of fluid through a pipe 622. It should be understood that actuator 160' controls the flow of fluid, while switch 642 controls power to motor 640. That is, the flow of fluid and power to motor 640 are controlled separately. In the described embodiment, body 116' does not serve as a reservoir for fluid, due to the electronics included in body 116'. Instead, fluid flows through pipe 622 and into fluid dispensing extension 118.

Pipe 622 is arranged to be coupled to fluid dispensing extension 118 through coupler 120' such that fluid may flow through pipe 622, through fluid dispensing extension 118, and out of fluid dispensing extension 118. As fluid dispensing extension 118 does not require a connection to motor 640, coupler 120' does not include a receptacle or receiving end for motor coupler 644.

When a fluid dispensing extension such as brush 514 of FIG. 5*b* is coupled to body 116', battery power generated using batteries 610 may serve to cause rotatable plate 520 to rotate. Specifically, motor 640 is arranged to cause rotatable plate 520 to rotate. Within brush 514, there may be a conduit which contains wiring that effectively couples motor 640 to rotatable plate 520 through motor coupler 640, as well as a tube which is arranged to be coupled to pipe 622. The wiring in the conduit enables power to reach rotatable plate 520 to cause rotatable plate 520 to rotate. It should be appreciated that the coupling of brush 514 to body 116' has not been shown purely for ease of illustration.

As shown in FIG. 6, nozzle subassembly 115' is arranged to be coupled to hose 114 of an overall spray nozzle system, e.g., spray nozzle system 100 of FIG. 1, through an adapter 620. It should be appreciated that hose 114 may, in one embodiment, be integrally coupled to body 116'. However, in the embodiment as shown, hose 114 is removably coupled to body 116'. Adapter 620 may generally take on a variety of different configurations. Such configurations include, but are not limited to, substantially fixably coupling a male adapter end 620*a* to hose 114 and substantially fixably coupling a female adapter end 620*b* to body 116' such that ends 620*a*, 620*b* may be snapped together. For such a configuration, both male adapter end 620*a* and female adapter end 620*b* are arranged to allow fluid to flow through hose 114, through male adapter end 620*a*, through female adapter end 620*b*, and into pipe 622.

As can be appreciated from the foregoing, the present invention, in one embodiment, addresses the problem of easily providing a maneuverable stream of fluid for cleaning, or other purposes, by providing a spray nozzle assembly that may be mechanically coupled to a water faucet. Such a spray nozzle assembly, which may be coupled to a faucet through an adapter, enables the temperature and the pressure of fluid to be readily varied using the faucet, while eliminating the need for either, or both, a pumping mechanism and a power source to be supplied in order to produce a maneuverable stream of fluid.

Although only a few embodiments of the present invention have been described, it should be understood that the present invention may be embodied in many other specific forms without departing from the spirit or the scope of the present invention. By way of example, although a spray nozzle has been described as being used with a filter and a sprayer, it should be appreciated that the spray nozzle may be used with only a filter or only a sprayer without departing from the spirit or the scope of the present invention.

The sprayer may generally either be specifically made for use as a part of a spray nozzle system, or the sprayer may be a standard spray bottle with a spray pumping mechanism, e.g., such as those that are commercially sold with many liquid cleaning products. In other words, a spray nozzle assembly may be adapted for use with a standard spray bottle for convenience.

Alternatively, a sprayer may be arranged to substantially automatically inject a solution contained within the sprayer into fluid provided by a faucet. For such a sprayer, it may become unnecessary for an individual to manually press a button or similar device to initiate a mixing of solutions.

In one embodiment, a spray nozzle may be used without either a water filter or a liquid sprayer. That is, the spray nozzle may be coupled substantially directly to a faucet using a handle, an adapter, and a hose or a tube. Such an assembly may be used when it is not necessary to filter the fluid flowing from the faucet. An adapter that is suitable for coupling a hose to faucet may, for example, be sized to accommodate faucets of various sizes.

While nozzle assembly has been described as including a body with a fluid dispensing extension that takes the shape of a nozzle, the fluid dispensing extension may have the configuration of a non-tapered tube, without departing from the spirit or the scope of the present invention. In addition, nozzle assembly may not necessarily include an actuator, as the controls provided with a water faucet may be sufficient to both start and stop the flow of water through the nozzle assembly.

It should be appreciated that although fluid dispensing extensions have been described as including tubes and various brushes, fluid dispensing extensions may also take on other configurations. By way of example, a fluid dispensing extension may have a pipe cleaner configuration that expels water in a stream from a tip of the pipe cleaner configuration.

Further, while the nozzle assembly and the adapter assembly have been described as being used for providing streams of water, the nozzle assembly and the adapter assembly may be used with numerous other fluid substances. These substances may include, but are not limited to, air, helium, and various liquid mixtures such as cleaning fluids or solvents.

A body of a nozzle subassembly has generally been described as including an actuator that controls the flow of fluid through the body and through a fluid dispensing extension. In one embodiment, the actuator may be a "two position" actuator which enables the flow of fluid to either be existent or non-existent. That is, the actuator may be an on-off switch. In another embodiment, the actuator may be further arranged to control the amount of fluid which flows through the body and the fluid dispensing extension, e. g., the actuator may be coupled to a graduated valve arrangement which allows for the partial opening of the valve.

An adapter assembly has been described as including a bypass valve that enables water to essentially bypass a fluid dispensing extension and flow substantially directly through the adapter assembly. In general, however, the adapter assembly may vary widely. For instance, a suitable adapter assembly may not include a bypass valve. When a bypass valve is not included in an adapter assembly that is coupled to a faucet, then a nozzle subassembly may be arranged such that a stream of fluid is substantially always expelled from the tip of a fluid dispensing extension unless fluid flow through the faucet is stopped, e.g., by turning a handle coupled to the faucet.

In an embodiment which does not include a dedicated filter, i.e., filter 110 of FIG. 1, the adapter assembly may include a filter. By way of example, the adapter assembly may include a mesh that filters particles from the fluid before the fluid passes out of the adapter assembly without departing from the spirit or the scope of the present invention.

Although a coupler that is suitable for coupling a fluid dispensing extension or a brush to a body of a nozzle subassembly has been described as being integral to the fluid dispensing extension or brush, it should be appreciated that the coupler may instead be integral to the body. Alternatively, the coupler may be separate from both the body and the fluid dispensing extension or brush, and may be arranged to couple to both the body and the fluid dispensing extension or brush. Therefore the described embodiments should be taken as illustrative and not restrictive, and the invention should be defined by the following claims and their full scope of equivalents.

What is claimed is:

1. An apparatus for dispensing a maneuverable stream of fluid, the fluid originating from a fluid source at a first pressure, the apparatus comprising:
   an adapter assembly, the adapter assembly being mechanically coupled to the fluid source, wherein the adapter assembly is arranged to allow the fluid to flow from the fluid source through the adapter assembly;
   a nozzle subassembly arranged to dispense the fluid at a second pressure, the nozzle subassembly including a fluid intake end and a fluid dispensing end, the fluid dispensing end being arranged to allow the fluid to flow therethrough in a stream-like configuration at the second pressure, wherein the fluid dispensing end is in fluid communication with the adapter assembly;
   a sprayer, the sprayer being in fluid communication with the adapter assembly and the nozzle subassembly, the sprayer being arranged to provide a solution, wherein the sprayer is further arranged to receive the fluid from the adapter assembly and to substantially mix the solution with the fluid, and wherein the sprayer is movable relative to the adapter assembly while maintaining fluid communication with the adapter assembly; and
   a flexible tubing arranged to carry the fluid and the solution, the flexible tubing having a first end and a second end, the second end of the flexible tubing being coupled to the fluid intake end of the nozzle subassembly.

2. An apparatus for dispensing a maneuverable stream of fluid according to claim 1 further including:
   a filter, wherein the filter is in fluid communication with the flexible tubing and the adapter assembly, the filter being arranged to allow the fluid to flow therethrough, the filter further being arranged to filter particulate matter from the fluid when the fluid flows therethrough.

3. An apparatus for dispensing a maneuverable stream of fluid according to claim 2 wherein the sprayer is in fluid communication with the filter and the nozzle subassembly, and the sprayer is further arranged to receive filtered fluid from the filter and to substantially mix the solution with the filtered fluid.

4. An apparatus for dispensing a maneuverable stream of fluid according to claim 3 wherein the sprayer is further arranged to provide the solution and the filtered fluid to the nozzle subassembly.

5. An apparatus for dispensing a maneuverable stream of fluid according to claim 2 wherein the adapter assembly includes a source filter arranged to filter at least some particles contained in the fluid when the fluid flows from the fluid source through the adapter assembly.

6. An apparatus for dispensing a maneuverable stream of fluid according to claim 2 wherein the filter is movable relative to the adapter assembly while maintaining fluid communication with the adapter assembly.

7. An apparatus for dispensing a maneuverable stream of fluid according to claim 1 wherein the sprayer is further arranged to substantially mix the solution with the fluid within the sprayer.

8. An apparatus for dispensing a maneuverable stream of fluid according to claim 1 wherein the fluid dispensing end is a nozzle tip, the nozzle tip including an elongated tapered tube-arrangement.

9. An apparatus for dispensing a maneuverable stream of fluid according to claim 1 wherein the fluid dispensing end includes one of a brush configuration and a polisher configuration.

10. An apparatus for dispensing a maneuverable stream of fluid according to claim 1 wherein the nozzle subassembly includes a pressure controller, the pressure controller being arranged to control the second pressure.

11. An apparatus for dispensing a maneuverable stream of fluid according to claim 1 wherein the fluid source is a faucet, and the adapter assembly includes:
- an outlet coupler, the outlet coupler being arranged to be coupled to the faucet;
- an inlet, the inlet being in fluid communication with the nozzle subassembly;
- an bypass outlet, the bypass outlet being arranged to permit the fluid to flow therethrough; and
- a valve, the valve being arranged to control the flow of the fluid through the inlet and the bypass outlet.

12. An apparatus for dispensing a maneuverable stream of fluid according to claim 11 wherein the nozzle subassembly further includes a push button controller arranged to control the flow of the stream-like configuration of fluid.

13. An apparatus for dispensing a maneuverable stream of fluid according to claim 12 wherein the valve of the adapter assembly is arranged to stop the flow of fluid through the inlet when the flow of fluid is prevented from flowing through the nozzle subsassembly via the push button controller.

14. An apparatus as according to claim 1 wherein the solution is a liquid.

15. An apparatus according to claim 1 wherein the sprayer includes a pump mechanism and a mix hose, the pump mechanism being arranged to pump the solution into the mix hose to substantially mix the solution with the fluid within the mix hose.

16. An apparatus for dispensing a maneuverable stream of fluid according to claim 1 further including a second flexible tubing arranged to carry the fluid between the adapter assembly and the sprayer.

17. An apparatus for dispensing a maneuverable stream of fluid according to claim 16 wherein one end of the second flexible tubing is releasably coupled to the adapter assembly.

18. An apparatus for dispensing a maneuverable stream of fluid according to claim 1 wherein the apparatus is a dental hygiene apparatus, and wherein a portion of the nozzle subassembly is arranged for insertion into a mouth.

19. A method for providing a maneuverable stream of fluid, the method comprising:
- providing a fluid to an adapter assembly from a fluid originating source, the adapter assembly being mounted to the fluid originating source;
- flowing the fluid from the adapter assembly to a filtering mechanism, wherein the filtering mechanism is movable relative to the adapter assembly when flowing the fluid from the adapter assembly;
- filtering the fluid with the filtering mechanism to remove at least some undesirable particles from the fluid;
- flowing the fluid from the filtering mechanism to a spraying mechanism, wherein the spraying mechanism is movable relative to the adapter assembly when flowing the fluid from the adapter assembly;
- mixing the fluid with a solution to form a mixed fluid in the spraying mechanism, the solution being provided by the spraying mechanism;
- flowing the mixed fluid from the spraying mechanism to a nozzle assembly;
- dispensing the mixed fluid through a fluid dispensing extension disposed in the nozzle assembly to form the stream of fluid.

20. A method as recited in claim 19 wherein the spraying mechanism is included in the nozzle assembly, the spraying mechanism further being arranged to receive the filtered fluid from the filtering mechanism and to mix the filtered fluid with the solution.

21. A method as recited in claim 19 wherein the solution is a water soluble solution.

22. A method as recited in claim 19 wherein the spraying mechanism is arranged to mix the fluid from the fluid source with the solution before the stream of fluid is dispensed by the fluid dispensing extension.

23. A method as recited in claim 19 wherein the fluid source is a faucet.

24. A method as recited in claim 19 wherein the fluid dispensing extension includes one of an elongated tapered tube and a brush.

25. A method as recited in claim 19 wherein the solution provided by the spraying mechanism is a liquid.

26. An apparatus for dispensing a small, maneuverable stream of fluid, the fluid originating from a fluid source at a first pressure, the apparatus comprising:
- an adapter assembly, the adapter assembly being mechanically coupled to the fluid source, wherein the adapter assembly is arranged to allow the fluid to flow from the fluid source through the adapter assembly;
- a filtering assembly, the filtering assembly including a solution reservoir that is arranged to provide a solution, wherein the filtering assembly is in fluid communication with the adapter assembly, the filtering assembly being arranged to filter particulate matter from the fluid when the fluid flows therethrough, the filtering assembly further being arranged to mix the solution with the filtered fluid;
- a nozzle subassembly arranged to dispense the mix of the filtered fluid and the solution at a second pressure, the nozzle subassembly including a fluid intake end and a fluid dispensing end, the fluid intake end being in fluid communication with the filtering assembly, the fluid dispensing end being arranged to allow the fluid to flow therethrough in a stream-like configuration at the second pressure, wherein the fluid dispensing end is in fluid communication with the adapter assembly; and
- a flexible tubing arranged to carry the fluid, the flexible tubing having a first end and a second end, the second end of the flexible tubing being coupled to the fluid intake end of the nozzle subassembly and the first end of the flexible tubing being coupled to the filtering assembly.

27. An apparatus according to claim 26 wherein the solution is a liquid.

28. An apparatus for dispensing a small maneuverable stream of fluid according to claim 26 further including a second flexible tubing arranged to carry the fluid, the second flexible tubing having a first end and a second end, the first end being coupled to the adapter assembly and the second end being coupled to the filtering assembly.

29. An apparatus for dispensing a maneuverable stream of fluid according to claim 28 wherein the first end of the second flexible tubing is releasable from the adapter assembly while the second end remains coupled to the filtering assembly.

30. An apparatus for dispensing a maneuverable stream of fluid according to claim 26 wherein the filtering assembly includes a cap for covering an opening in the filtering assembly, the cap being removably attached to the filtering assembly so that a filter cartridge can be removed through the opening in the filtering assembly.

31. An apparatus for dispensing a maneuverable stream of fluid according to claim 26 wherein the filtering assembly is movable relative to the adapter assembly while maintaining fluid communication with the adapter assembly.

32. An apparatus for dispensing a small maneuverable stream of fluid according to claim 26 wherein the apparatus is a dental hygiene apparatus, and wherein a portion of the nozzle subassembly is arranged for insertion into a mouth.

33. A system for dispensing a maneuverable stream of fluid, the fluid originating from a fluid source at a first pressure, the apparatus comprising:

an adapter assembly configured for mechanically coupling to the fluid source, and having a valve, a first dispensing path and a second dispensing path, the valve being configured to move between a first position, allowing the fluid to flow through the first dispensing path, and a second position, allowing the fluid to flow through the second dispensing path;

a filter assembly in fluid communication with the adapter assembly, the filter assembly being arranged to allow the fluid to flow therethrough and to filter particulate matter from the fluid when the fluid flows therethrough, and having a filter intake and a filter dispensing end, the filter assembly being movable relative to the adapter assembly;

a first flexible tube configured for carrying the fluid between the adapter assembly and the filter assembly, and having a first end configured for mechanically coupling to the second dispensing path of the adapter assembly, and a second end for mechanically coupling to the filter intake;

a sprayer assembly in fluid communication with the filter assembly, the sprayer assembly being arranged to allow the fluid to flow therethrough, to store a solution therein and to mix the solution with the fluid when the fluid flows therethrough, the sprayer assembly having a sprayer intake and a sprayer dispensing end;

a nozzle assembly in fluid communication with the sprayer assembly, the nozzle assembly being arranged to allow the mixed fluid to flow therethrough and to dispense the mixed fluid in a stream like fashion at a second pressure, the nozzle assembly having a nozzle intake and a nozzle dispensing end, the nozzle assembly being movable relative to the sprayer assembly; and a second flexible tube configured for carrying the fluid between the sprayer assembly and the nozzle assembly, and having a first end configured for mechanically coupling to the sprayer dispensing end of the sprayer assembly, and a second end for mechanically coupling to the nozzle intake.

34. The system as recited in 33 wherein the first end of first flexible tube is releasable from the second dispensing path of the adapter assembly so as to allow the filter assembly to be removed from the adapter assembly.

35. The system as recited in 33 wherein the nozzle assembly includes a push button configured to move between a first position, allowing the mixed fluid to flow through the nozzle dispense end, and a second position, preventing the mixed fluid from flowing through the nozzle dispense end.

36. The system as recited in 35 wherein the valve of the adapter assembly is configured to automatically move to the first position when the push button of the nozzle assembly is in the second position to prevent the fluid from flowing to the filter.

37. The system as recited in 35 wherein the nozzle assembly includes a rotatable head, a motor for moving the rotatable head, and a switch for activating the motor.

38. The system as recited in 37 therein the switch and the push button are independently controlled by a user so as to allow the flow of the fluid with rotation of the head, the flow of the fluid without the rotation of the head, and the rotation of the head without the flow of the fluid.

39. The system as recited in 35 wherein the rotatable head includes a brush.

* * * * *